US012397459B2

(12) United States Patent
Terwey et al.

(10) Patent No.: US 12,397,459 B2
(45) Date of Patent: Aug. 26, 2025

(54) SYSTEMS AND METHODS FOR A SLITTER ASSEMBLY

(71) Applicant: PACESETTER, INC., Sylmar, CA (US)

(72) Inventors: Russ Terwey, Saint Michael, MN (US); Bradley Knippel, Lino Lakes, MN (US)

(73) Assignee: PACESETTER, INC., Sylmar, CA (US)

(*) Notice: Subject to any disclaimer, the term of this patent is extended or adjusted under 35 U.S.C. 154(b) by 0 days.

(21) Appl. No.: 18/665,391

(22) Filed: May 15, 2024

(65) Prior Publication Data
US 2024/0383164 A1 Nov. 21, 2024

Related U.S. Application Data

(60) Provisional application No. 63/467,214, filed on May 17, 2023.

(51) Int. Cl.
B26D 3/00 (2006.01)
A61M 25/00 (2006.01)

(52) U.S. Cl.
CPC ......... B26D 3/001 (2013.01); A61M 25/0097 (2013.01)

(58) Field of Classification Search
None
See application file for complete search history.

(56) References Cited

U.S. PATENT DOCUMENTS

| | | | |
|---|---|---|---|
| 4,997,424 A * | 3/1991 | Little | A61M 25/0668 604/161 |
| 6,497,681 B1 * | 12/2002 | Brenner | A61M 25/0668 604/524 |
| 7,615,057 B2 * | 11/2009 | Andrews | A61M 25/00 606/108 |
| 7,678,101 B2 | 3/2010 | Sage | |
| 8,042,273 B2 * | 10/2011 | Drake | B26D 3/001 604/164.05 |
| 8,529,544 B2 | 9/2013 | Haarala et al. | |
| 10,350,408 B2 | 7/2019 | Wood et al. | |
| 11,458,285 B2 | 10/2022 | Graham et al. | |
| 11,938,288 B2 | 3/2024 | Hauck et al. | |
| 2003/0158565 A1 * | 8/2003 | Gardeski | B26D 3/001 606/167 |
| 2008/0082079 A1 | 4/2008 | Braga et al. | |
| 2009/0049698 A1 * | 2/2009 | Drake | A61M 25/0668 30/282 |
| 2010/0094226 A1 * | 4/2010 | Helgeson | A61M 25/0097 600/585 |
| 2012/0227561 A1 * | 9/2012 | Grauhan | B26D 7/02 83/456 |
| 2015/0065872 A1 * | 3/2015 | Drake | A61N 1/0587 600/432 |
| 2024/0383164 A1 * | 11/2024 | Terwey | A61M 25/0097 |

* cited by examiner

Primary Examiner — Hwei-Siu C Payer
(74) Attorney, Agent, or Firm — Armstrong Teasdale LLP

(57) ABSTRACT

Systems and methods for slitting a delivery device are described. A slitter assembly for slitting the delivery device in accordance with the present disclosure includes a housing, a lock mechanism coupled to the housing, and a clamshell mechanism coupled to the lock mechanism. The clamshell mechanism defines a channel having an adjustable diameter and sized to receive a device. The slitter assembly also includes a blade configured to slit a tubular shaft of the delivery device.

16 Claims, 10 Drawing Sheets

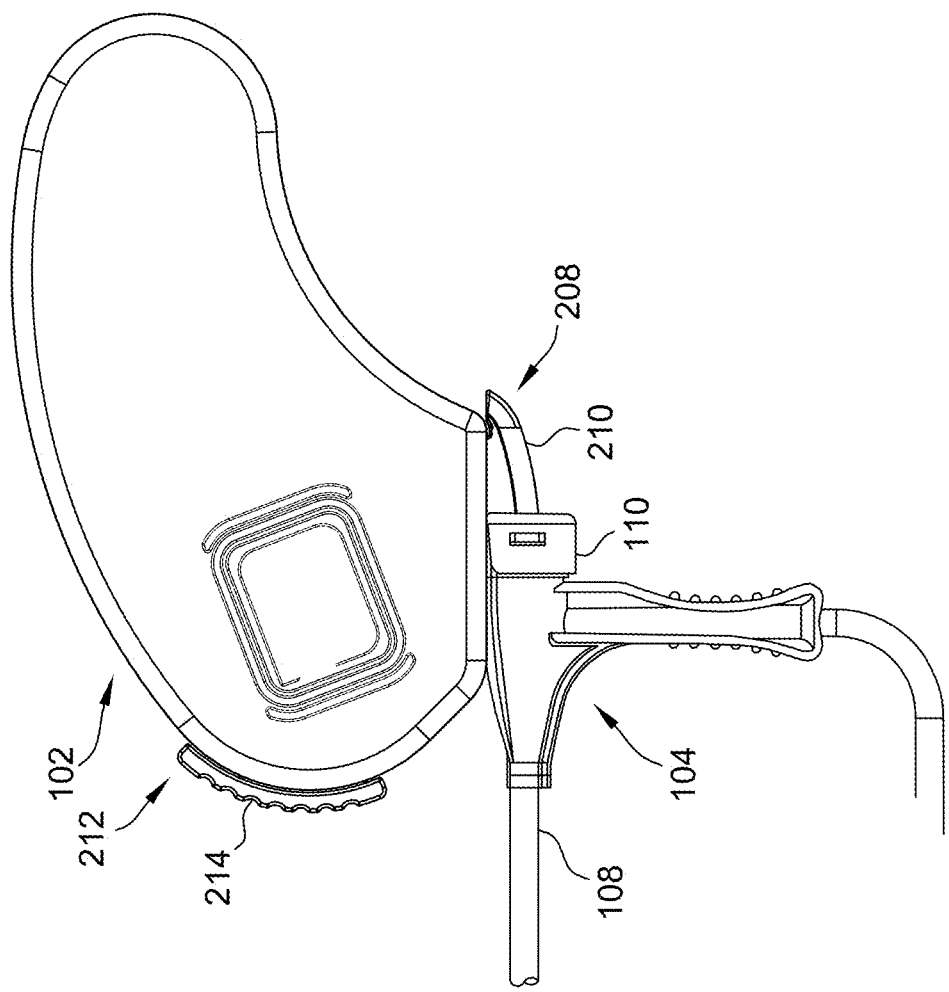

SYSTEMS AND METHODS FOR A SLITTER ASSEMBLY

CROSS-REFERENCE TO RELATED APPLICATIONS

This application claims priority to U.S. Provisional Patent Application No. 63/467,214 filed on May 17, 2023, which is incorporated by reference herein in its entirety.

FIELD OF THE DISCLOSURE

The present disclosure relates generally to a slitter assembly. In particular, the present disclosure relates to systems and methods for a slitter assembly used to slit tubular bodies.

BACKGROUND

Catheter or sheath systems are widely used in the medical industry for various procedures. Such systems include tubular bodies typically made from materials such as silicone, polyurethane, or nylon. In some cases, it is necessary to split the tubular bodies lengthwise in order to expose their corresponding lumens and enable the removal of the tubular bodies from a patient. For example, catheter and sheath systems may be utilized to deliver a left ventricular (LV) lead of a cardiac resynchronization therapy (CRT) system into the coronary sinus of a patient for implantation. In order to enable the tubular body to be removed from the implanted lead and from within the patient once implantation is complete, the tubular body may be longitudinally slit. To facilitate the slitting/splitting of a tubular body, several medical systems offer separate dedicated slitting/splitting tools. In use, these tools are aligned with and placed onto the lead after a hemostasis valve at the proximal end of the tubular body is manually split. The slitting/splitting tool is then slid over the lead until the tool's tip encounters the tubular body. The tool is then secured to the lead and the tubular body is withdrawn from the patient and over the tool, thereby slitting/splitting the tubular body and enabling the tubular body to be removed off of the lead without inadvertent lead dislodgement.

Because the aforementioned slitting/splitting tools are aligned with, placed on, and secured to the lead extending through the tubular body, these tools may make it difficult to remove the tubular body. Accordingly, systems and methods for improved slitting/splitting a tubular body of a catheter or sheath are desirable.

BRIEF SUMMARY OF THE DISCLOSURE

In one aspect, the present disclosure is directed to a slitter assembly including a housing, a lock mechanism coupled to the housing, and a clamshell mechanism coupled to the lock mechanism. The clamshell mechanism defines a channel having an adjustable diameter and sized to receive a device. The slitter assembly also includes a blade configured to slit a tubular shaft of a delivery device.

In another aspect, the present disclosure is directed to a method for slitting a delivery device. The method includes capturing a device within a channel of a clamshell mechanism of a slitter assembly. At least a portion of the device is held in a tubular shaft of the delivery device. The method also includes pulling the delivery device through a blade of the slitter assembly while the slitter assembly and the device are stationary within the clamshell mechanism.

The foregoing and other aspects, features, details, utilities, and advantages of the present disclosure will be apparent from reading the following description and claims, and from reviewing the accompanying drawings.

BRIEF DESCRIPTION OF THE DRAWINGS

FIGS. 7A-7C are schematic diagrams of one embodiment of the slitter assembly of FIG. 2A interacting with a delivery device.

DETAILED DESCRIPTION OF THE DISCLOSURE

The present disclosure provides systems, devices, and methods for a slitter assembly used to slit tubular bodies. The slitter assembly in accordance with the present disclosure includes a blade and a clamshell mechanism coupled to the slitter assembly. The slitter assembly also includes a ramp and a lock mechanism coupled to the clamshell mechanism and the ramp. The lock mechanism includes a lever, at least one tab, and a lock feature, and is configured to expand and collapse the clamshell mechanism.

It is generally known that various medical procedures, using catheter and sheath systems, require that the tubular bodies of these systems be split (e.g., to enable removal of the tubular bodies from a patient's body). To split the tubular bodies, slitting/splitting tools may be used. However, at least some known splitting/splitting tools must be aligned with, placed on, and secured to a lead extending through a lumen of the tubular body, which may make the tubular body removal process difficult.

As used herein, the terms "proximal" and "distal," refer to a direction relative to a user of a delivery device. "Proximal" refers to a direction toward the end of the delivery device near to the user, and "distal" refers to a direction away from the user and (generally) inside the body of a patient. As used herein, the terms "substantially," "generally," and "about" are intended to mean that slight deviations from absolute are included within the scope of the term so modified.

Figure 1:
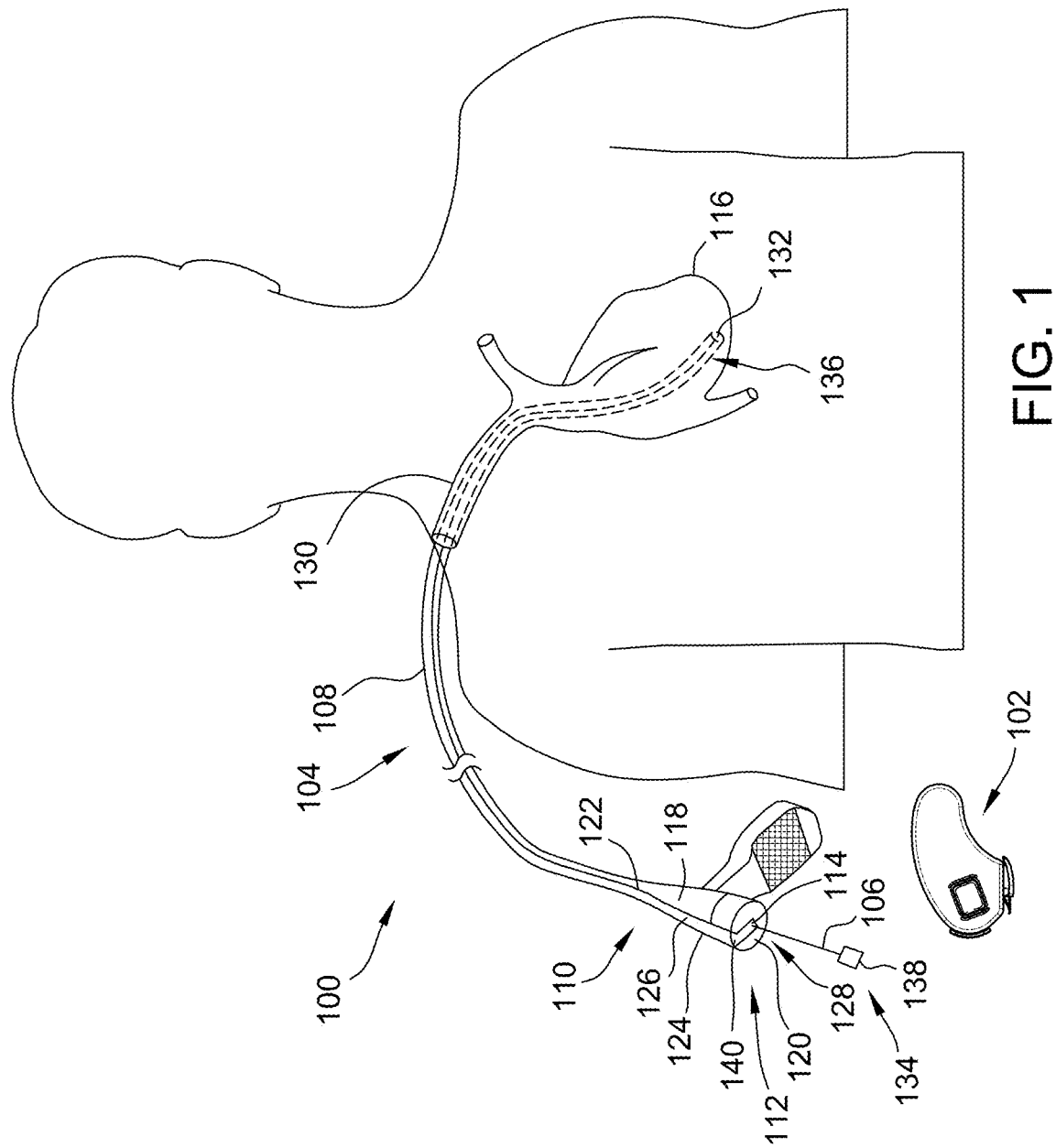
FIG. 1 is a schematic diagram of a medical device system including a slitter assembly that may be used for delivering an implantable medical device (IMD) into a patient's body.

FIG. 1 is a schematic diagram of a medical device system 100 used for delivering an implantable medical device (IMD) into a patient's body. In general, system 100 includes a slitter assembly 102 and a delivery device 104 (e.g., a catheter or sheath) configured to deliver an implantable device 106 into a patient's body. Device 106 may include an implantable medical device such as an implantable medical lead, an inner catheter or outer sheath, an introducer, a stylet, a guidewire, a sensor, or other accessories or devices typically delivered via delivery device 104. Delivery device 104 may have a tubular shaft 108 and a hub 110 on a proximal end 112 of delivery device 104. Tubular shaft 108 may include a lumen 114 extending the length of tubular shaft 108. Lumen 114 provides a passageway for device 106 to enter the body, for example, the patient's heart 116 during implantation of device 106 (e.g., a lead). Upon placement of device 106, delivery device 104 may be removed from device 106 by slitting delivery device 104, and in particular tubular shaft 108, along its length.

In one embodiment, tubular shaft 108 is integrated into hub 110 such that an inner wall of tubular shaft 108 forms a longitudinally extending strip of a wall 118 of hub 110. The longitudinal length of wall 118 extends from a proximal end 120 of hub 110 to a distal end 122 of hub 110. Accordingly, the material forming tubular shaft 108 may extend the length of delivery device 104 uninterrupted and fully accessible to a slitting tool, such as slitter assembly 102, through the length of hub 110. When using slitter assembly 102 to slit delivery device 104 along its length, including the lengths of tubular shaft 108 and hub 110, slitter assembly 102 may encounter material of tubular shaft 108 without encountering material of hub 110, thereby enabling delivery device 104 to be slit and removed from the device 106 without disrupting device 106. For example, deliver device may be slit and removed from device 106 while device 106 remains stationary. Hub 110 includes a hemostasis valve 124 and a slitting path 126 (e.g., an integrated longitudinally extending shaft strip) that reduces a hub-to-shaft transitional jerk that may occur, thereby reducing complications associated with dislodging a placed lead or other device 106, such as increased procedure time or damage to cardiac tissue. A cap 128 and hemostasis valve 124 may be coupled to hub 110, and cap 128 may retain hemostasis valve 124 within hub 110.

During implantation of device 106, tubular shaft 108 may be inserted into the patient's heart 116 via the subclavian vein 130, as shown. Alternatively, and in other embodiments, the tubular shaft 108 may be inserted into the patient's heart 116 via a femoral vein (not shown) or other suitable entry point to the patient's body. Once tubular shaft 108 is in position, device 106 may be inserted therethrough. For example, once tubular shaft 108 is in position, device 106, such as a lead, may be inserted through hemostasis valve 124 in hub 110 and through lumen 114 of tubular shaft 108 so that a distal tip 132 (e.g., a lead tip) at the distal end of the device 106 may be guided into position in the patient's heart 116.

Device 106 includes a proximal end 134 and a distal end 136. In one embodiment, proximal end 134 includes an electrical connector 138 for mechanically and electrically coupling proximal end 134 to an IMD, such as a pulse generator (e.g., pacemakers, defibrillators, or implantable cardioverter defibrillators (ICD)). Electrical connector 138 is sized to prevent delivery device 104 from being proximally withdrawn from device 106. Once device 106 is implanted or placed into position, as appropriate, delivery device 104 may be slit to enable delivery device 104 to clear electrical connector 138 or proximal end 134 as delivery device 104 is removed from device 106.

As mentioned above, the material forming tubular shaft 108 extends into hub 110 to form at least a longitudinal strip of wall 118 of hub 110. Therefore, slitting path 126 for slitting delivery device 104, including tubular shaft 108 and hub 110, extends along shaft material and does not encounter hub material, or at least any significant amount of hub material. With respect to slitting path 126, delivery device 104 has no hub-to-shaft transition. In other words, because tubular shaft 108 is integrated into hub 110, delivery device 104 does not require removal of hub 110 in order to slit tubular shaft 108.

Once device 106 is implanted or placed at the desired location, delivery device 104 may be slit with slitter assembly 102. As discussed above, cap 128 and hemostasis valve 124 may be coupled to hub 110. In some embodiments, an arcuate opening 140 in cap 128 is configured to enable passage of a slitter blade of slitter assembly 102 through cap 128 and hemostasis valve 124 such that removal of the cap 128 prior to slitting is not required. Also, hemostasis valve 124 may be slit while in place within hub 110. Slitter assembly 102 is configured to (a) facilitate capturing of device 106 using a clamshell mechanism of slitter assembly 102, (b) cover and protect device 106 during the slitting process while delivery device 104 is separated from device 106, and (c) easily slit delivery device 104 by providing a slitter blade including an angle ranging between 10 and 50 degrees that may reduce the force used to slit delivery device 104. As a result, slitter assembly 102 enables slitting with low and consistent slit forces along the length of delivery device 104, substantially reducing, if not completely eliminating, the transition jerk. The possibility of dislodging or disrupting the position of device 106 is thereby reduced or eliminated.

Figure 2A:
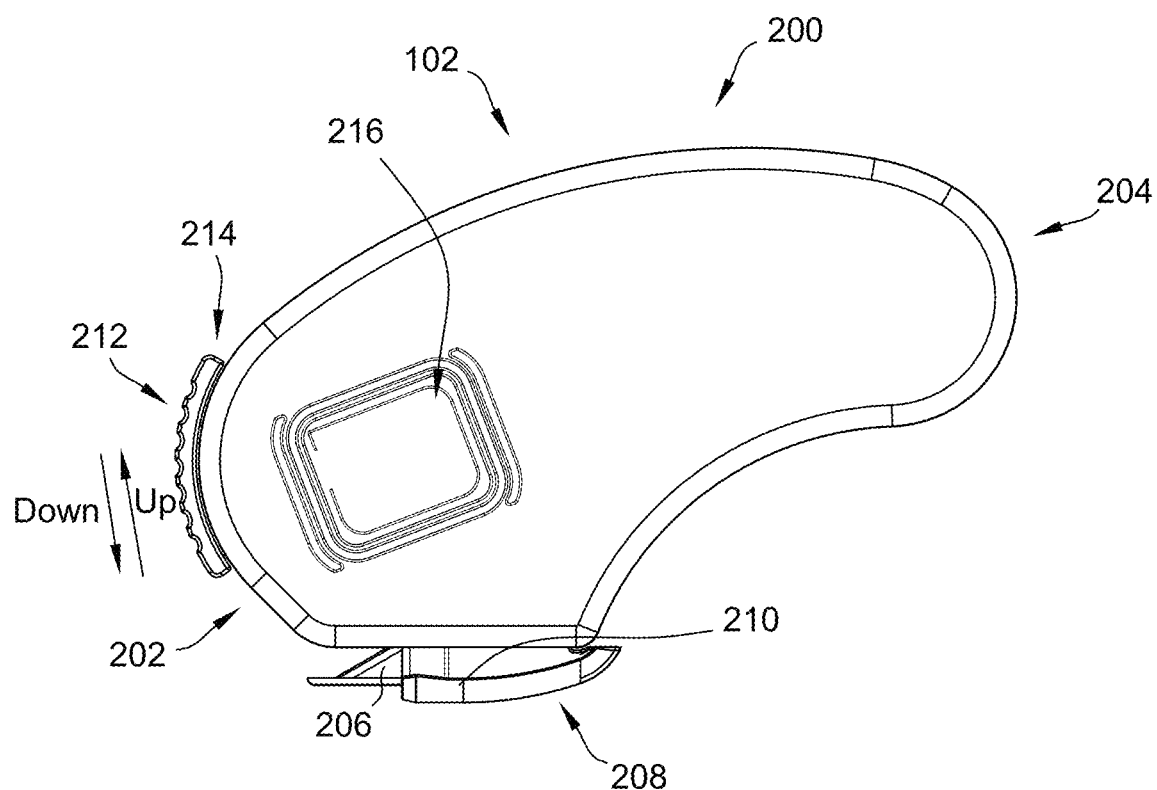
FIG. 2A is a side view of one embodiment of a slitter assembly.

FIG. 2A is a side view of one embodiment of slitter assembly 102. Slitter assembly 102 includes a housing 200, a distal section 202 and a proximal section 204. Distal section 202 includes a blade 206 and a clamshell mechanism 208 coupled to blade 206. Clamshell mechanism 208 may be made of plastic material, such as Acrylonitrile Butadiene Styrene (ABS) plastic, to enable secure capturing of device 106, as described herein. Clamshell mechanism 208 defines a channel 210 covering a portion of blade 206 and a portion of device 106 (shown in FIG. 1). When using slitter assembly 102 to slit delivery device 104 (shown in FIG. 1) along its length, device 106 is introduced into channel 210, such that blade 206 may slit the lengths of tubular shaft 108 and hub 110 (both shown in FIG. 1) and delivery device 104 may be removed from the device 106 without disrupting device 106.

Distal section 202 also includes a lock mechanism 212 coupled to the clamshell mechanism. Lock mechanism 212 includes a lever 214, and is configured to selectively expand and collapse clamshell mechanism 208, in particular channel 210. By collapsing and expanding clamshell mechanism 208, different diameter sizes of device 106 may be accommodated within channel 210. In other words, the diameter of channel 210 is adjustable. The outer diameter size of channel 210 may be range between about 0.120 inches (0.30 cm) in a closed position and about 0.200 inches (0.51 cm) in an open position. The inner diameter of channel 210 may be in an oval shape that may clamp or receive up to a 6 French (about 2 mm) lead. The inner diameter size of channel 210 may range between about 0.060 inches (0.15 cm) in a closed position and 0.138 inches (0.35 cm) in an open position. In other words, when clamshell mechanism 208 is closed, the inner diameter of channel 210 may be about 60 thousandth of an inch (about 0.15 cm), thereby enabling channel 210 to clamp a 4 French (about 0.13 cm) lead. As a result, slitter assembly 102 provides an active capture feature to securely hold and encapsulate different diameters of device 106 during the slitting process, thereby reducing, if not completely eliminating, the transition jerk, damage to proximal and distal ends of delivery device 104, and the possibility of dislodging or disrupting the position of device 106.

Distal section 202 of housing 200 further includes a thumb location 216 that guides a clinician to hold slitter assembly 102 with either hand of the clinician, while placing the clinician's thumb on thumb location 216. This hand position encourages axial alignment with delivery device 104 during the slitting process.

Figure 2B:
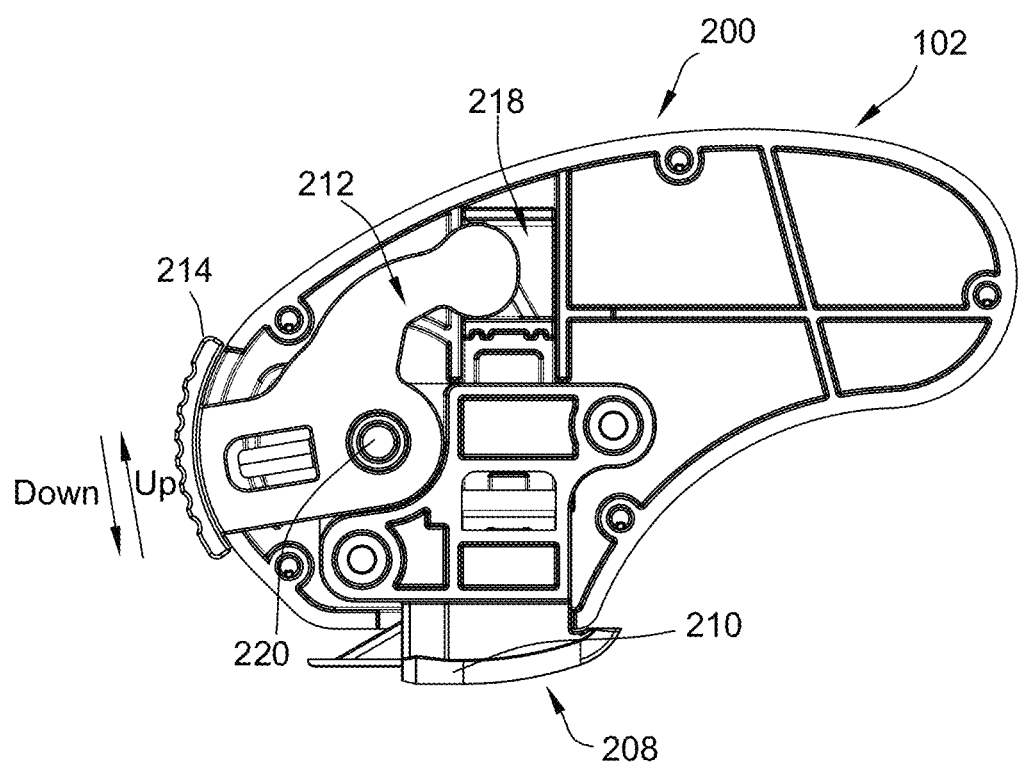
FIG. 2B is a sectional view of the slitter assembly of FIG. 2A.

FIG. 2B is a sectional view of slitter assembly 102 shown in FIG. 2A. In addition to the components of slitter assembly 102 described in FIG. 2A, slitter assembly 102 includes a ramp 218 coupled to lock mechanism 212. Ramp 218 activates (e.g., moves or translates) in response to lever 214 changing its position. In other words, ramp 218 is driven by the position (e.g., up, down) of lever 214. By changing the position of lever 214, a portion of lock mechanism 212 pivots within the interior of housing 200, causing a far end of lock mechanism 212 to pivot about a housing pin 220. The end of the lock mechanism 212 is shaped so as to engage an end of ramp mechanism 218, causing ramp mechanism 218 to translate linearly within housing 200 to open/close clamshell mechanism 208.

When ramp 218 activates, clamshell mechanism 208 moves from a first configuration to a second configuration. For example, when lever 214 is in a down position as further shown in FIG. 3A, clamshell mechanism 208 is open. In another example, when lever 214 is in an up position as shown further in FIG. 3B, clamshell mechanism 208 is closed. In general, when lever 214 is down and clamshell mechanism 208 is open, device 106 (shown in FIG. 1) may be introduced into channel 210. Once device 106 is placed in channel 210, lever 214 may be moved up so that clamshell mechanism 208 starts closing until clamshell mechanism 208 stops closing, thereby capturing device 106 (e.g., capturing device 106 at about the diameter of device 106). At this point with device 106 contained within closed channel 210, a clinician may start slitting delivery device 104 to remove delivery device 104 from device 106. Since device 106 is held firm within channel 210 of clamshell mechanism 208, the possibility of dislodging or disrupting the position of device 106 is reduced or eliminated during the slitting process. Upon removal of delivery device 104, lever 214 may be moved to the down position to open clamshell mechanism 208 and remove device 106 from slitter assembly 102.

Figure 3A:
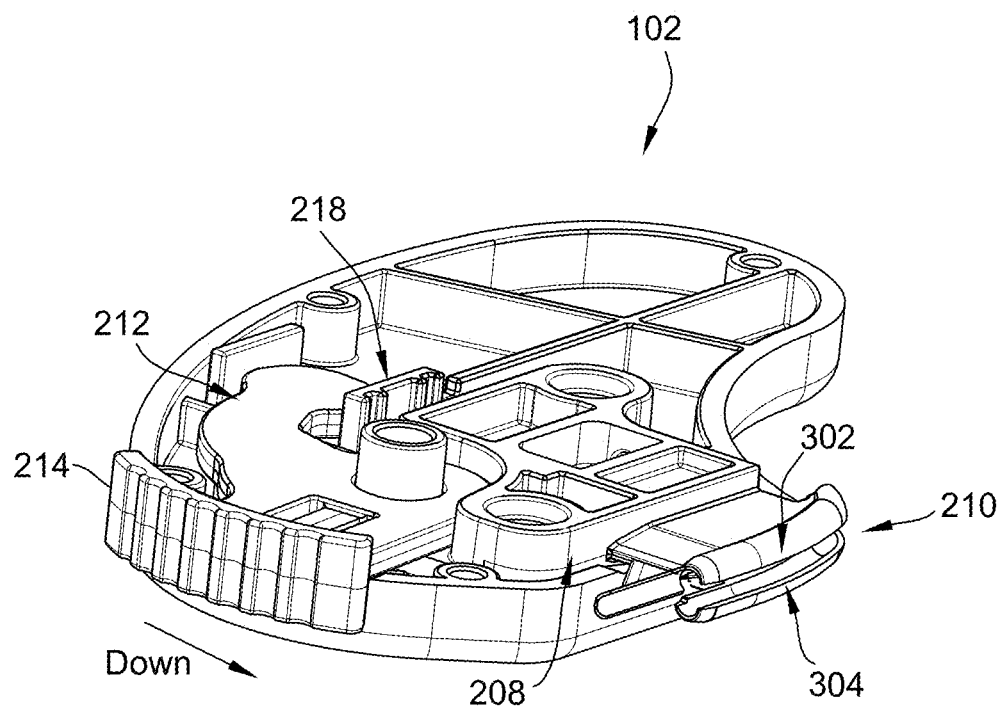
FIG. 3A is a perspective view of the slitter assembly of FIG. 2B in a first configuration.

FIG. 3A is a sectional view of slitter assembly 102 shown in FIG. 2B in a first configuration. In the first configuration, lever 214 is down and clamshell mechanism 208, and in particular, channel 210, is open. Clamshell mechanism 208 includes a top side 302 and a bottom side 304 forming channel 210. Top side 302 is positioned opposite to bottom side 304. When channel 210 moves from an open position to a closed position, or vice versa, only one of top side 302 or bottom side 304 moves to open or close channel 210. For example, if top side 302 is movable, then bottom side 304 is stationary, and vice versa. As mentioned above, lock mechanism 212 is coupled to a ramp 218, such that ramp 218 activates in response to lever 214 changing its position. When ramp 218 activates, clamshell mechanism 208 moves from the first configuration (e.g., open) to a second configuration (e.g., closed). In particular, ramp 218 moves the movable side of channel 210. In other words, ramp 218 moves one of top side 302 or bottom side 304, whichever is coupled to ramp 218, to close channel 210. In general, channel 210 moves from the open configuration to the closed configuration once device 106 (shown in FIG. 1) is placed into channel 210.

Figure 3B:
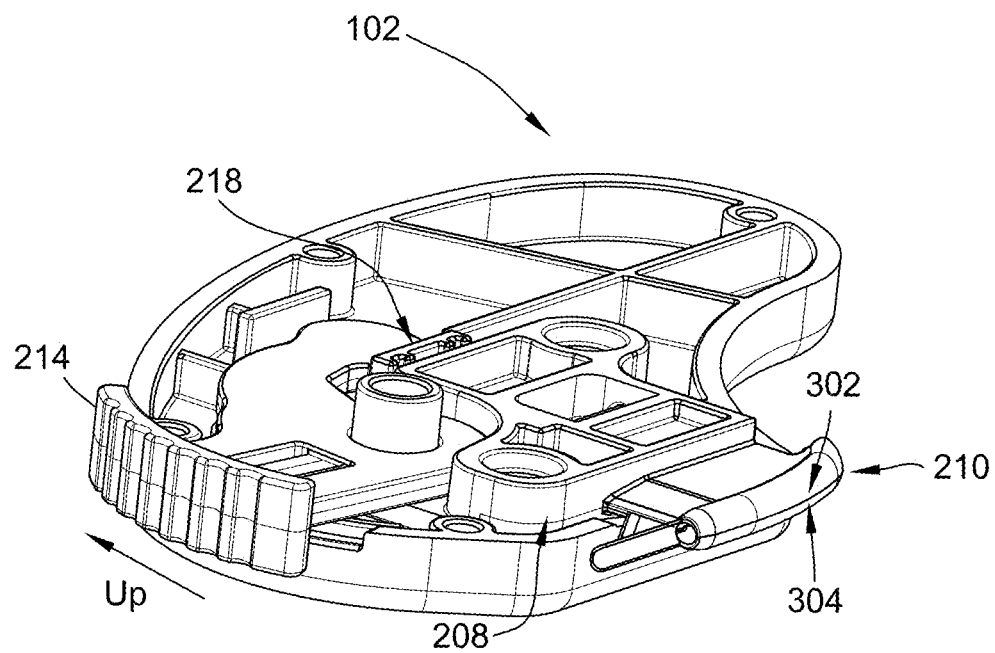
FIG. 3B is a perspective view of the slitter assembly of FIG. 2B in a second configuration.

FIG. 3B is a sectional view of slitter assembly 102 shown in FIG. 2B in a second configuration. In the second configuration, lever 214 is up and clamshell mechanism 208 is closed, in particular channel 210. As described above, only one of top side 302 or bottom side 304 is movable. When ramp 218 activates, clamshell mechanism 208 moves from the second configuration (e.g., closed) to the first configuration (e.g., open). In particular, ramp 218 moves the movable side of channel 210. In other words, ramp 218 moves one of top side 302 or bottom side 304, whichever is coupled to ramp 218, to open channel 210. In general, channel 210 moves from the open configuration to the closed configuration once device 106 (shown in FIG. 1) is placed into channel 210.

Figure 4:
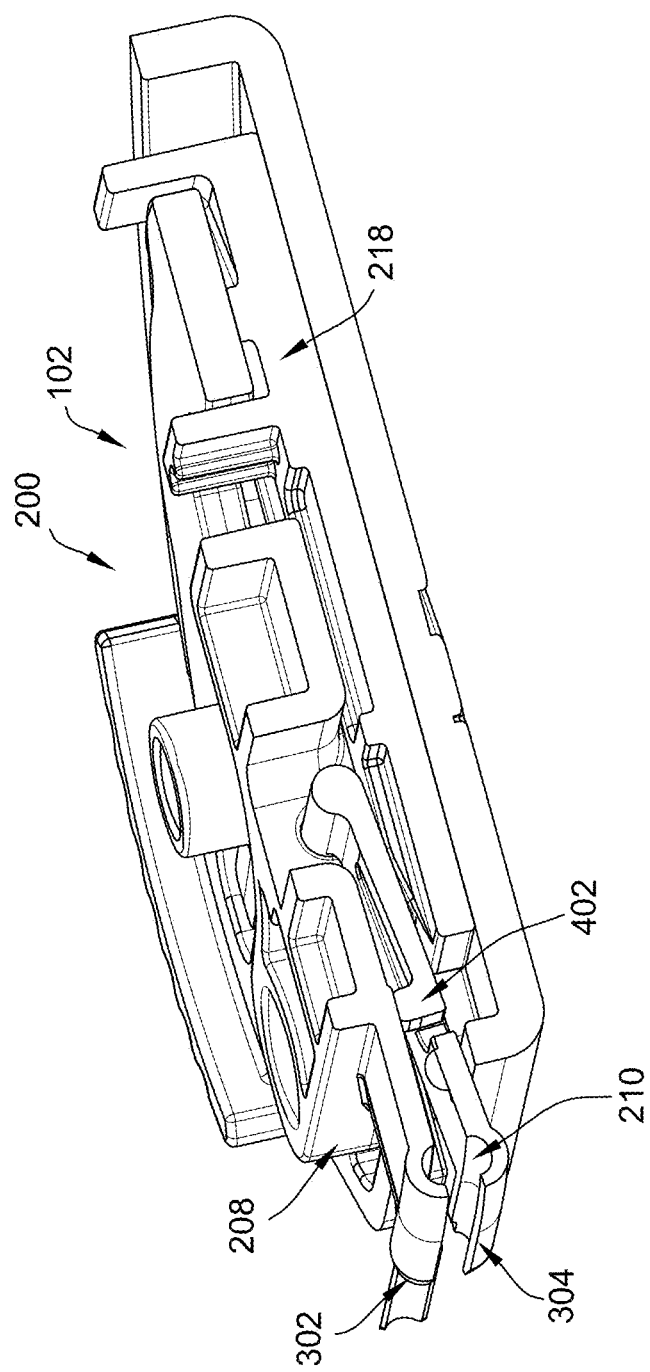
FIG. 4 is a perspective view of a clamshell mechanism of the slitter assembly of FIG. 2A.

FIG. 4 is a perspective view of clamshell mechanism 208 of slitter assembly 102. As described above, when ramp 218 activates, clamshell mechanism 208 moves from one configuration to another (e.g., from an open configuration to a closed configuration, or vice versa). In one embodiment, bottom side 304 is movable and top side 302 is stationary, where ramp 218 is coupled to bottom side 304 and is located under bottom side 304. Bottom side 304 includes a tab 402 coupled to ramp 218 and top side 302. In this embodiment, when ramp 218 translates downwardly within housing 200, tab 402 pivots about a pivot pin (not shown) connected to housing 200, pushing tab 402 towards the stationary portion (e.g., bottom side 304) of clamshell mechanism 208 and causing clamshell mechanism 208 to actuate.

In one example, when ramp 218 activates, ramp 218 moves away (e.g., retracts) from bottom side 304. By moving away from bottom side 304, ramp 218 releases a portion of bottom side 304, including tab 402, thereby causing channel 210 to open. In another example, when ramp 218 activates, ramp 218 moves toward bottom side 304, such that ramp 218 supports a portion of bottom side 304, including tab 402, thereby causing channel 210 to close. In some embodiments, a spring element may be coupled to ramp 218 and bottom side 304 of clamshell mechanism 208. The spring element may bias ramp 218 and may assist in pushing ramp 218 back when lever 214 is moved to a down position. In other embodiments, a release mechanism may be coupled to ramp 218 and bottom side 304, and perform similar functions to those of tab 402, as described herein. In yet other embodiments, other mechanisms may be used in combination with ramp 218 to enable channel 210 to open and close, as described herein.

Figure 5A:
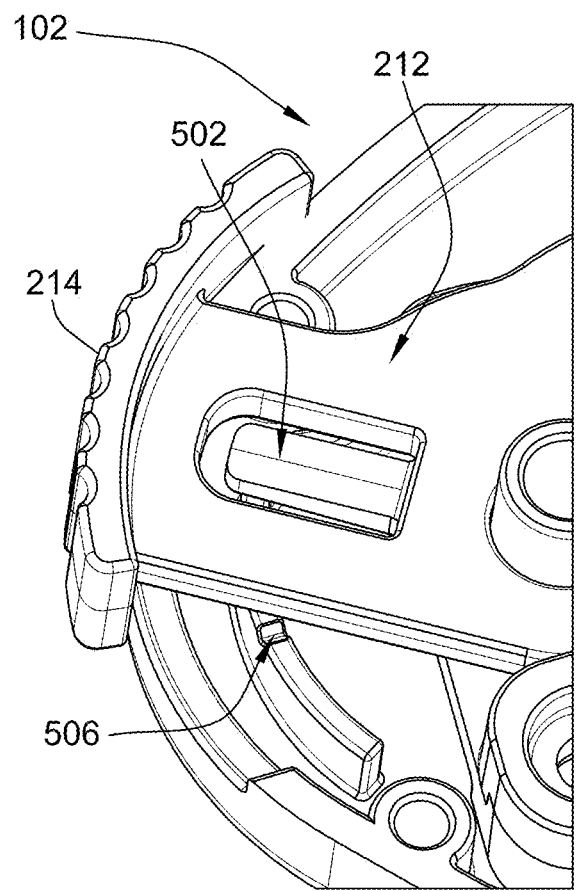
FIG. 5A is a perspective view of a lock mechanism of the slitter assembly of FIG. 2A.
Figure 5B:
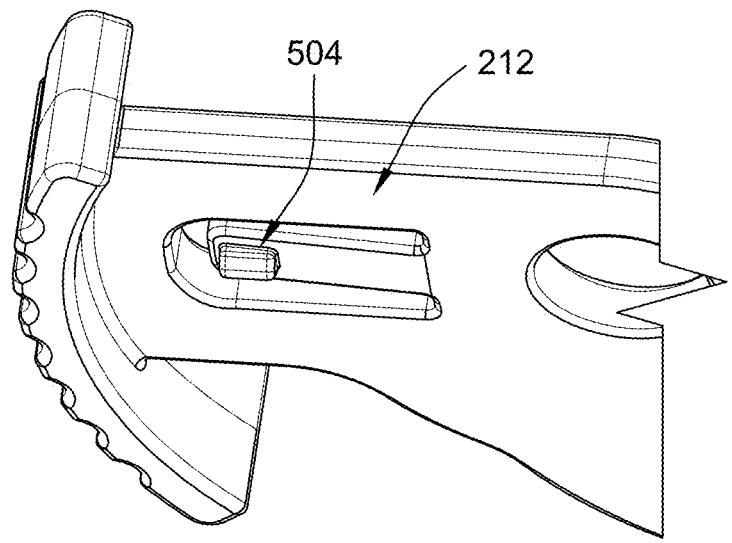
FIG. 5B is another perspective view of a lock mechanism of the slitter assembly of FIG. 2A.

FIGS. 5A and 5B are perspective views of lock mechanism 212 of slitter assembly 102. In addition to lever 214, lock mechanism 212 includes a lock tab 502 and a lock feature 504. In one embodiment, lock feature 504 may include a V lock feature, which may be a mechanism that uses low force to flex up a plastic feature (e.g., lock tab 502 and/or lock feature 504) during movement, and flex back down the plastic feature into grooves (e.g., lock grooves 506 described in detail below) that restrict movement. In particular, lock feature 504 may include a bendable tab (e.g., the V lock feature) that pivots at its base to permit a detent feature that engages with a corresponding lock groove 506 when lock mechanism 212 is in either a fully open (e.g., lever 214 is in the down direction) or fully closed position (e.g., lever 214 is in the up direction). A force in either the up or down direction (depending on whether lever 214 is in the open or closed position) causes the bendable tab to deflect slightly and enables a detent of lock feature 504 to disengage from the corresponding lock groove 506, thereby allowing lever 214 and lock mechanism 212 to move to another position. Lock feature 504 may be made of flexible material that enables engaging and disengaging from lock grooves 506. Lock feature 504 is configured to bend at its base and displace to permit the detent to disengage from lock groove 506 by applying low force to flex up the plastic feature (e.g., tab 502 and/or lock feature 504) during movement. In other embodiments, lock feature 504 may include other suitable lock features that enable lock mechanism 212 to function, as described herein.

FIG. 5A shows a top view of lock mechanism 212, and FIG. 5B shows a bottom view of lock mechanism 212. In one embodiment, lock feature 504 locks lever 214 at a desired position by engaging with one of a plurality of lock grooves 506 of slitter assembly 102. Lock grooves 506 are positioned under lock tab 502 and lock feature 504. For example, when lever 214 is changed from an open configuration (shown in FIG. 4) to a closed configuration, lock feature 504 may disengage from a lock groove 506 for opening channel 210, move to another lock groove 506, and engage in the other lock groove 506, causing lock mechanism 212 to close channel 210. In one embodiment, the plurality of lock grooves 506 includes two lock grooves 506 (e.g., one lock groove 506 for opening channel 210 and another lock groove 506 for closing channel 210). In other embodiments, the plurality of lock grooves 506 includes more than two lock grooves 506, where each lock groove 506 may specify a particular diameter for channel 210.

Figure 6:
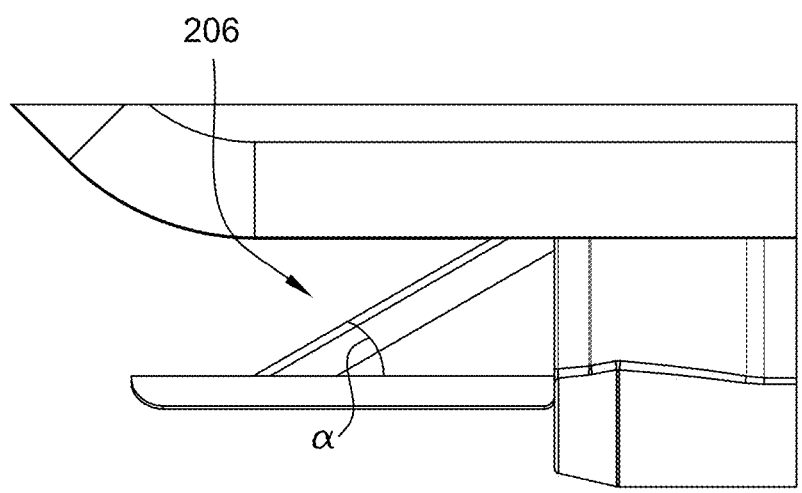
FIG. 6 is a sectional view of a slitter of the slitter assembly of FIG. 2A.

FIG. 6 is a sectional view of an example blade 206 of slitter assembly 102 (shown in FIG. 2A). As described above, blade 206 is coupled to clamshell mechanism 208 (shown in FIG. 2A), where a portion of clamshell mechanism 208 includes channel 210 (shown in FIG. 2A) covering a portion of blade 206 and a portion of device 106 (shown in FIG. 1). In one embodiment, the cutting edge of blade 206 includes an angle α that may range between 10 and 50 degrees (e.g., angle α may be 30 degrees) with respect to a horizontal base of blade 206. Angle α enables a shallower entry of delivery device 104, in particular tubular shaft 108 (both shown in FIG. 1), in comparison to conventional blades, which include an angle of about 60 degrees. A shallow entry of delivery device 104 permits easily slitting delivery device 104 by reducing the force required to slit delivery device 104.

Figure 7A:
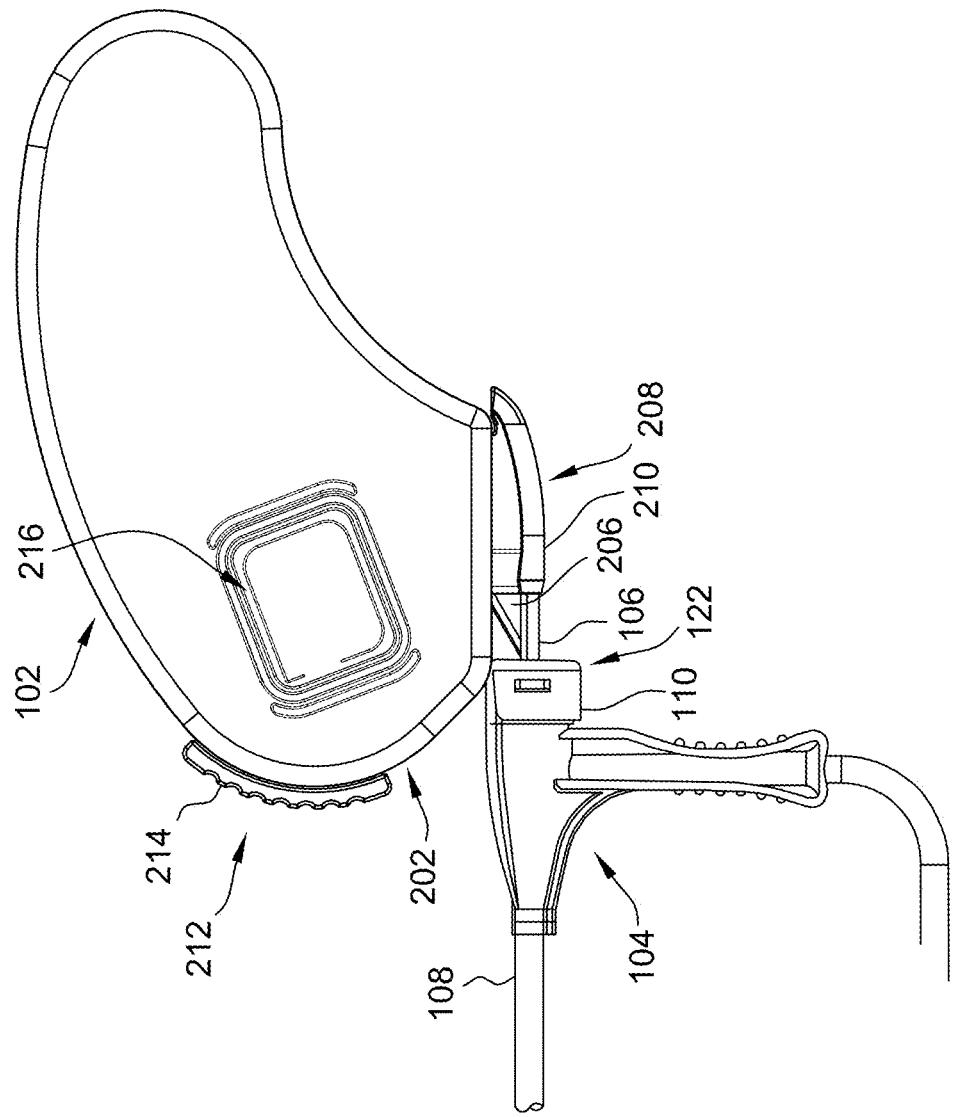
Figure 7C:
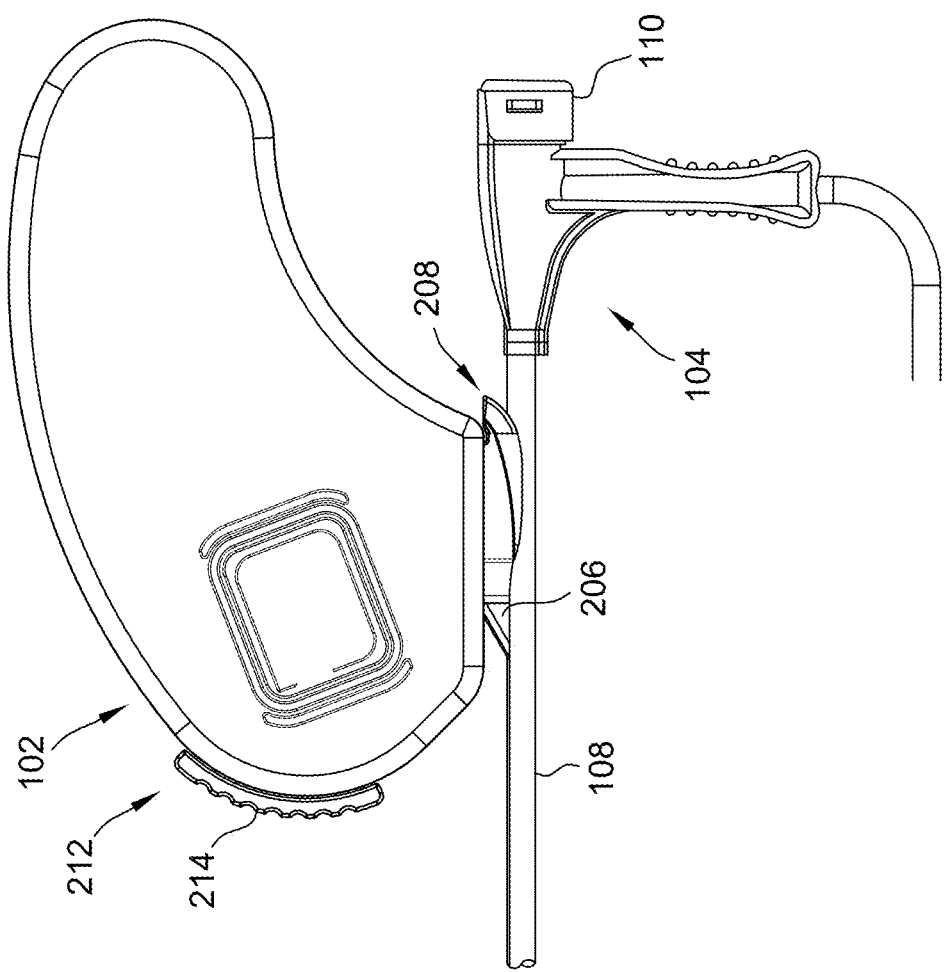

FIGS. 7A-7C are schematic diagrams of one embodiment of slitter assembly 102 interacting with delivery device 104. As shown in FIG. 7A, the slitting process may be initiated by introducing device 106 into clamshell mechanism 208. Clamshell mechanism 208 may partially cover device 106 and blade 206. In particular, device 106 is introduced into channel 210 of clamshell mechanism 208. Device 106 is also introduced into arcuate opening 140 (shown in FIG. 1) in distal end 122 of hub 110 of delivery device 104, such that device 106 may be introduced into tubular shaft 108 of delivery device 104. Device 106 may be in contact with blade 206. When using slitter assembly 102 to slit delivery device 104 along its length, device 106 is introduced into channel 210 and the opening in distal end 122 of hub 110, such that blade 206 may slit the lengths of tubular shaft 108 and hub 110 and delivery device 104 may be removed from the device 106 without disrupting device 106.

FIG. 7B shows slitter assembly 102 in a subsequent step to the initiation of the slitting process shown in FIG. 7A. In FIG. 7B, clamshell mechanism 208 and channel 210 are introduced into delivery device 104. Specifically, device 106 and blade 206 (both shown in FIG. 7A) are introduced into arcuate opening 140 (shown in FIG. 1) in hub 110 and tubular shaft 108. During this subsequent step, lock mechanism 212 and lever 214 are in a lock position to securely hold and encapsulate device 106 within channel 210 during the slitting process.

FIG. 7C shows slitter assembly 102 in a step subsequent to the step shown in FIG. 7B. In FIG. 7C, delivery device 104 is pulled through blade 206 while slitter assembly 102 and device 106 (shown in FIG. 7A) remain stationary during the slitting process. Similar to FIG. 7B, lock mechanism 212 and lever 214 are in a lock position to securely hold and encapsulate device 106 within channel 210. As described above, blade 206, positioned in clamshell mechanism 208, slits tubular shaft 108 along the length of tubular shaft 108 to remove tubular shaft 108 and delivery device 104 from device 106 (shown in FIG. 7A). By doing so, the slitting process substantially reduces, if not completely eliminates, the transition jerk. The possibility of dislodging or disrupting the position of device 106 is thereby reduced or eliminated.

Figure 8:
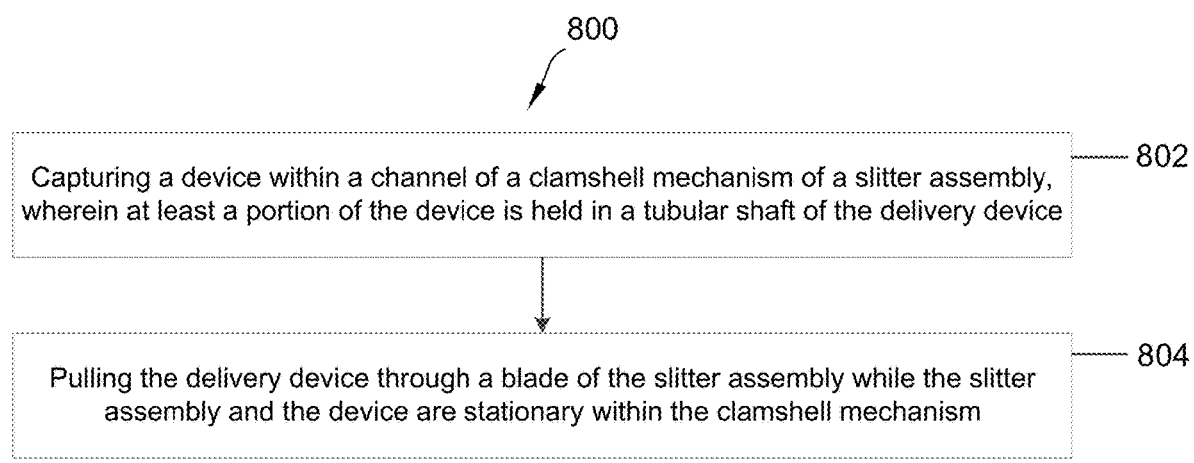
FIG. 8 is flow diagram of a method of slitting a delivery device.

FIG. 8 is flow diagram of a method 800 of slitting a delivery device 104 (shown in FIG. 1). Method 800 may be implemented, for example, by slitter assembly 102 (shown in FIG. 2A). Method 800 includes capturing 802 device 106 within channel 210 of clamshell mechanism 208 (both shown in FIG. 7A) of slitter assembly 102. At least a portion of device 106 is held in tubular shaft 108 (shown in FIG. 7A) of delivery device 104. As described herein, the diameter of channel 210 is adjustable, enabling different sizes (e.g., diameter sizes) of device 106 to be captured. The sizes of device 106 may vary as device 106 may include an implantable medical lead, an inner catheter or outer sheath, an introducer, a stylet, a guidewire, a sensor, or other accessories or devices typically delivered via delivery device 104, as described herein.

Method 800 also includes pulling 804 delivery device 104 through blade 206 (shown in FIG. 7A) of slitter assembly 102 while slitter assembly 102 and device 106 are stationary. Pulling 804 may include, for example, slitting tubular shaft 108 along a length of tubular shaft 108 to remove device 106 from delivery device 104.

It should be understood that method 800 may include additional and/or alternative steps to those set forth above. For example, in some embodiments, method 800 may also include activating ramp 218 when lever 214 (both shown in FIG. 3A) transitions between different position, and in response to activating ramp 218, method 800 further includes opening or closing channel 210 of clamshell mechanism 208, or causing, by lock tab 502 (shown in FIG. 502), one side of channel 210 to open or close channel 210. In addition, in other embodiments, method 800 may include receiving, a lock groove 506 (shown in FIG. 7A), lock feature 504 (shown in FIG. 7B), and locking channel 210 in an open configuration or a closed configuration. In yet other embodiments, method 800 may include moving, using lever 214, lock feature 504 from one lock groove 506 to another lock groove 506.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like)

are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A slitter assembly comprising:
   a housing;
   a lock mechanism coupled to the housing, wherein the housing comprises a plurality of lock grooves, each lock groove configured to receive a lock feature of the lock mechanism;
   a clamshell mechanism coupled to the lock mechanism, wherein the clamshell mechanism defines a channel having an adjustable diameter and sized to receive a device, and wherein the lock mechanism is configured to lock the channel in an open configuration or a closed configuration depending upon which one of the lock grooves engages with the lock feature; and
   a blade configured to slit a tubular shaft of a delivery device.

2. The slitter assembly of claim 1, wherein the lock mechanism comprises a lever and a ramp, and wherein the ramp is configured to be activated when the lever transitions between different positions.

3. The slitter assembly of claim 2, wherein the ramp is coupled to the clamshell mechanism, and wherein when the ramp is activated, the clamshell mechanism opens or closes the channel.

4. The slitter assembly of claim 2, wherein the clamshell mechanism comprises a lock tab coupled to the ramp and one of two sides of the channel, and wherein when the ramp is activated, the lock tab causes the one side of the channel to open or close the channel.

5. The slitter assembly of claim 1, wherein an outer diameter of the channel ranges between 0.51 cm in the open configuration and 0.30 cm in the closed configuration.

6. The slitter assembly of claim 1, wherein an inner diameter of the channel ranges between 0.35 cm in the open configuration and 0.15 cm in the closed configuration.

7. The slitter assembly of claim 1, wherein a cutting edge of the blade forms an angle greater than or equal to 10 degrees and equal to or less than 50 degrees with respect to a horizontal base of the blade.

8. The slitter assembly of claim 1, wherein the lock mechanism comprises a lever coupled to the lock feature, and wherein the lever is operable to move the lock feature from one lock groove of the plurality of lock grooves to another lock groove of the plurality of lock grooves.

9. A method for slitting a delivery device, the method comprising providing a slitter assembly including a housing, and a lock mechanism coupled to the housing, wherein the housing includes a plurality of lock grooves, each lock groove configured to receive a lock feature of the lock mechanism;
   capturing a device within a channel of a clamshell mechanism of the slitter assembly, wherein at least a portion of the device is held in a tubular shaft of the delivery device, and wherein the channel has an adjustable diameter and sized to receive the device, and wherein the capturing comprises (a) receiving, at one of the plurality of lock grooves, the lock feature and (b) locking the channel in an open configuration or a closed configuration using the lock feature; and
   pulling the delivery device through a blade of the slitter assembly while the slitter assembly and the device are stationary, wherein the blade is configured to slit the tubular shaft of the delivery device.

10. The method of claim 9, wherein pulling the delivery device through the blade further comprises slitting the tubular shaft along a length of the tubular shaft to remove the device from the delivery device.

11. The method of claim 9, wherein the a lock mechanism includes a lever and a ramp, and wherein the ramp is coupled to the clamshell mechanism, and wherein the method further comprises:
    activating the ramp when the lever transitions between different positions; and
    in response to activating the ramp, opening or closing the channel of the clamshell mechanism.

12. The method of claim 11, wherein the clamshell mechanism includes a lock tab coupled to the ramp and one of two sides of the channel, and wherein the method further comprises, in response to activating the ramp, causing, by the lock tab, the one side of the channel to open or close the channel.

13. The method of claim 9, further comprising providing the channel to have an outer diameter range between 0.51 cm in an open configuration and 0.30 cm in a closed configuration, and providing the channel to have an inner diameter range between 0.35 cm in the open configuration and 0.15 cm in the closed configuration.

14. The method of claim 9, further comprising providing the blade with a cutting edge having an angle greater than or equal to 10 degrees and equal to or less than 50 degrees with respect to a horizontal base of the blade.

15. The method of claim 9, further comprising providing the delivery device to include a hub having an arcuate opening configured to receive the clamshell mechanism.

16. The method of claim 9, wherein the lock mechanism includes a lever coupled to the lock feature, and wherein the method further comprises moving, using the lever, the lock feature from one lock groove of the plurality of lock grooves to another lock groove of the plurality of lock grooves.

* * * * *